United States Patent [19]

Koehler et al.

[11] Patent Number: 5,359,082
[45] Date of Patent: Oct. 25, 1994

[54] PREPARATION OF 4-SUBSTITUTED IMIDAZOLES FROM N-FORMYL-α-AMINONITRILE

[75] Inventors: Ulrich Koehler, Mannheim; Thomas-Michael Kahl, Roemerberg; Horst Neuhauser, Dudenhofen; Hardo Siegel, Speyer; Michael Kroener, Mannheim, all of Fed. Rep. of Germany

[73] Assignee: BASF Aktiengesellschaft, Ludwigshafen, Fed. Rep. of Germany

[21] Appl. No.: 36,032

[22] Filed: Mar. 23, 1993

[30] Foreign Application Priority Data

Mar. 26, 1992 [DE] Fed. Rep. of Germany ....... 4209847

[51] Int. Cl.$^5$ .................. C07D 233/58; C07D 233/56; C07D 233/54
[52] U.S. Cl. ..................... 548/335.1; 564/215
[58] Field of Search ....................... 548/335.1; 564/215

[56] References Cited

U.S. PATENT DOCUMENTS

| | | | |
|---|---|---|---|
| 2,226,057 | 12/1940 | Graenacher et al. | 548/335.1 |
| 2,399,601 | 4/1946 | Kyrides et al. | 548/335.1 |
| 2,710,870 | 6/1955 | Lawson | 548/335.1 |
| 3,255,200 | 6/1966 | Green | 548/335.1 |
| 3,388,132 | 6/1968 | Kroeper et al. | 548/335.1 |
| 4,284,781 | 8/1981 | Sze | 548/335.1 X |
| 4,340,744 | 7/1982 | Schwarz et al. | 548/335.1 |
| 4,409,389 | 10/1983 | Bellas et al. | 548/335.1 |
| 4,927,942 | 5/1990 | Speranza et al. | 548/335.1 |

FOREIGN PATENT DOCUMENTS

| | | | |
|---|---|---|---|
| 025191 | 3/1981 | European Pat. Off. | 548/335.1 |
| 0036519 | 9/1981 | European Pat. Off. | 548/335.1 |
| 2748976 | 5/1979 | Fed. Rep. of Germany | 548/335.1 |
| 3009631 | 9/1981 | Fed. Rep. of Germany | 548/335.1 |
| 3009605 | 10/1981 | Fed. Rep. of Germany | 548/335.1 |
| 2926405 | 11/1964 | Japan | 548/335.1 |
| 1380304 | 1/1975 | United Kingdom | 548/335.1 |

*Primary Examiner*—Floyd D. Higel
*Attorney, Agent, or Firm*—Keil & Weinkauf

[57] ABSTRACT

A process for the preparation of 4-substituted imidazoles of the general formula

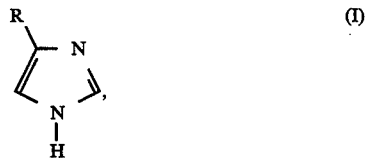

in which
R denotes $C_1$–$C_{20}$ alkyl, $C_3$–$C_{20}$ cycloalkyl, aryl, and $C_7$–$C_{20}$ aralkyl,
wherein
a) N-formyl-α-aminonitriles of the general formula I

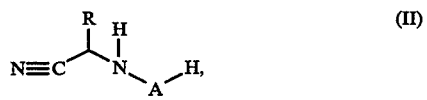

in which R has the meanings stated above and A stands for carbonyl, are reacted, at a temperature ranging from 20° to 200° C. and a pressure ranging from 20 to 500 bar, with hydrogen in the presence of hydrogenation catalysts and
b) the resulting N-formyl-1,2-diamines of the general formula

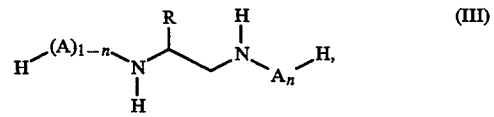

in which R and A have the meanings stated above and n stands for 0 or 1, are reacted over a cyclization/dehydrogenation catalyst at a temperature ranging from 200° to 600° C. and a pressure ranging from 0.001 to 5 bar.

4 Claims, No Drawings

PREPARATION OF 4-SUBSTITUTED IMIDAZOLES FROM N-FORMYL-α-AMINONITRILE

The present invention relates to a process for the preparation of 4-substituted imidazoles by catalytic hydrogenation of N-formyl-α-aminonitriles under super-atmospheric pressure over hydrogenation catalysts followed by reaction of the N-formyl-1,2-aliamines obtained over cyclization/dehydrogenation catalysts at elevated temperatures.

Processes for the preparation of imidazoles by intramolecular cyclization followed by dehydrogenation of N,N'-bisformyl-1,2-diamines using Ni/Mo, Co/Mo or Zn catalysts in the gas phase are disclosed in DE-A 3,009,605 and EP-A 25,191. In such cases 4-methylimidazole is obtained at a yield of ca 70%. However, this method suffers from the drawback that the bisformyl compound must first be prepared in an upstream stage (eg, using methyl formate), and a formyl group (as co) is again lost during subsequent cyclization.

The said disadvantage of a multistage synthesis is all the more pronounced when the process directly follows on the previous preparation of imidazolines (DE-A 2,748,976; DE-A 4 3,009,631;U.S. Pat. No. 4,927,942).

It is thus an object of the present invention to overcome the aforementioned disadvantages.

Accordingly, we have found a novel and improved process for the preparation of a 4-substituted imidazole of the general formula

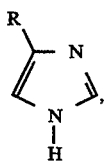

in which
R denotes $C_1$–$C_{20}$ alkyl, $C_3$–$C_{20}$ cycloalkyl, aryl, or $C_7$–$C_{20}$ aralkyl,
wherein
a) an N-formyl-α-aminonitrile of the general formula

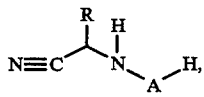

in which n has the meanings stated above and A stands for carbonyl, is reacted, at a temperature ranging from 20° to 200° C. and a pressure ranging from 20 to 500 bar, with hydrogen in the presence of a hydrogenation catalyst and
b) the resulting N-formyl-1,2-diamine of the general formula

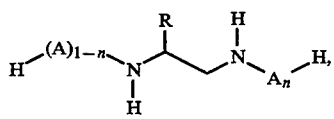

in which R and A have the meanings stated above and n stands for 0 or 1, is reacted over a cyclization/dehydrogenation catalyst at a temperature ranging from 200° to 600° C. and a pressure ranging from 0.001 to 5 bar.

The process of the invention may be carried out as follows:

a) The N-formyl-α-aminonitriles II used for the process are readily obtainable compounds and can be prepared in a simple manner, eg, by cyanohydrin synthesis as disclosed in DE-A 1,950,280.

The hydrogenation of the nitrile group can be carried out either by the use of complex metal hydrides such as lithiumtrialkoxyaluminum hydrides (cf Milos Hudlick'y, Ed. in *Organic Chemistry*, Ellis Horwood Ltd., 1986, pp. 173 to 175), or preferably catalytically using heterogeneous catalysts, eg, metals such as Fe, Co, Ni, Pt, Pd, Rh, and Nu. In the case of hydrogenation effected using a heterogeneous catalyst it is preferred to operate under relatively high hydrogen pressures in the liquid phase, ie, at pressures ranging from 20 to 500 bar and more preferably from 50 to 300 bar and temperatures of from 20° to 200° C. and more preferably from 40° to 120° C. Excessively high temperatures and excessively long reaction times should be avoided in order to prevent deformylation.

The catalysts used in the process of the invention can be used either in the form of supported catalysts or in solid form, ie, without supports. The nature of the substrate is not usually of decisive importance. Usual supporting materials can be used such as silicon dioxide, aluminum oxides, titanium dioxides, activated charcoal, silicates, or zeolites. Binding agents or molding agents can also be used, if necessary, for the preparation of the catalysts.

As a general rule, the catalysts are preferably activated with hydrogen prior to use. The active catalyst components present after calcination, normally in the form of their oxides, are reduced to a major extent, usually to the corresponding metals. Further details on the preparation of these catalysts can be taken from DE-A 2,321,101 and DE-A 3,904,083.

The catalytic hydrogenation of the N-formyl-α-aminonitriles II by means of hydrogen and heterogeneous catalysts can be effected as a batch process in stirred autoclaves or as a continuous process in cascades of stirred autoclaves or in tubular reactors of conventional design, which can be operated by methods involving packed bubble columns or trickle columns. The hydrogenation catalyst can be suspended in the reaction mixture, or alternatively used as a fixed bed in the reactor. The hydrogenation can take place in a solvent, eg, toluene, xylene, tetrahydrofuran, dioxane, methanol, ethanol, diethyl ether, methyl-tert-butyl ether, dimethylformamide, N-methylpyrrolidone, and others in the absence of, but preferably in the presence of, from I to 50 mol % of ammonia per mole of II. The presence of a solvent is unnecessary for the execution of the hydrogenation. Particularly preferred catalytically active metals are Fe, Co, and Ni.

b) Prior to conversion to the 4-substituted imidazoles I, separation of the solvent by distillation and, optionally, purification, eg, by distillation, of the hydrogenation product is possible but not essential. Certain solvents showing a tendency in the gas phase to undergo alkylation (eg, methanol, ethanol) should be removed, however.

In order to prevent the resulting imidazoles I from crystallizing out on leaving the reaction zone, it might be advantageous to dilute the N-formyl-1,2-diamines III used with a solvent which is substantially inert under the conditions of the reaction.

Suitable solvents which are substantially inert under the conditions of the reaction are, eg, water or ethers such as tetrahydrofuran and dioxane.

The cyclization/dehydrogenation reaction can be carried out, preferably, in a gas phase fixed bed or fluid bed reactor. It is feasible to carry out the reaction in the liquid phase. For the preferred gas phase method, the process is carried out at temperatures between 200° and 600° C. and preferably between 280° and 450° C. and pressures ranging from 0.001 to 5bar, preferably from 0.02 to 1.5 bar and more preferably under a pressure of 1 bar (atmospheric pressure), optionally in a stream of $H_2$ Or $H_2/CO$. It is, of course, possible to precede the actual dehydrogenation reaction with a cyclization step effected over an acid catalyst to form the imidazoline, eg, using acid heterogeneous catalysts such as zeolites, eg, aluminum silicate zeolites, boron silicate zeolites, iron silicate zeolites, gallium silicate zeolites, and silicalites of the pentasil, faujasite, X, or Y type or acid metal salts and acid metal oxides, eg, phosphates, hydrogen phosphates, dihydrogen phosphates, and pyrophosphates and any other phosphates of the elements Ca, Ba, St, Al, Fe, and Zr with and without any additions of $SiO_2$, $TiO_2$, and $Al_2O_3$ (including as supporting material) and oxides of the elements Mo and W. Other suitable catalysts for this purpose are, eg, those listed in EP-A 12,371.

It is much more economical, however, if, in compliance with the present invention, the cyclization and dehydrogenation of the N-formyl-1,2-diamines III is carried out in a single stage. Suitable catalysts are the dehydrogenation catalysts disclosed, in principle, in the literature, which contain Group IVb, Vb, VIb, VIIb, VIII, Ib, and IIb elements, such as Cr, Mo, Fe, Ru, Co, Rh, Ni, Pd, Pt, Cu, Ag, Zn, and Cd, whilst Ni, Co, Fe, Mo, Zn, Cu, Ag, Cr, Pt, Pd, or mixtures thereof are preferred. Solid or supported catalysts can be used. If use is made of supported catalysts, suitable supporting materials, in addition to those already mentioned with respect to the hydrogenation catalysts (loc cit), are alkaline-earth metal oxides and alkaline-earth metal carbonates, lanthanum oxides, and lanthanum carbonates. Possibly, the use of acid supporting materials (as described above) can have a favorable influence on space-time yield and selectivity. The catalytically active components can be used as oxides (eg, ZnO) or in the form of their metals (eg, Pd). When use is made of the metallic form, activation of the metal in a stream of hydrogen for a number of hours at temperatures between 250° and 600° C. is advantageous.

The crude product obtained by cyclization and dehydrogenation can, finally, be freed, by distillation, from any solvent added and be purified by distillation, crystallisation, or chromatography.

The substituents R and A and the index n in the compounds I, II, and III have the following values:

R $C_1$-$C_{20}$ alkyl and preferably $C_1$-$C_{12}$alkyl such as methyl, ethyl, n-propyl, isopropyl, n-butyl, isobutyl, sec-butyl, tert-butyl, n-pentyl, isopentyl, secpentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl, and isododecyl and more preferably $C_1$-$C_4$ alkyl such as methyl, ethyl, n-propyl, isopropyl. n-butyl, isobutyl, sec-butyl, and tert-butyl, $C_3$-$C_{20}$ cycloalkyl and preferably $C_3$-$C_8$ cycloalkyl such as cyclopropyl, cyclobutyl, cyclopentyl, cyclohexyl, cycloheptyl, and cyclooctyl and more preferably cyclopentyl, cyclohexyl, and cyclooctyl, aryl such as phenyl, 1-naphthyl, 2-naphthyl, 1-anthryl, 2-anthryl, and 9-anthryl and preferably phenyl, 1-naphthyl, and 2-naphthyl and more preferably phenyl, $C_7$-$C_{20}$ aralkyl and preferably $C_7$-$C_{20}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl, and 4-phenylbutyl and more preferably benzyl, 1-phenethyl, and 2-phenethyl,

A carbonyl n 0 or 1.

4-Substituted imidazoles I are important intermediates, eg, for the preparation of pharmaceuticals (, eg, Cimetidin).

EXAMPLES

EXAMPLE 1

Hydrogenation of N-formylalanine nitrile

In a stirred autoclave having a capacity of 10 L there were placed 200 g of Raney nickel and 1000mL of tetrahydrofuran, and 1275g of ammonia (75mol) were added following a nitrogen purge. 30 bar of hydrogen were forced in, and the mixture was heated to 60° C. and the pressure increased to 200 bar of $H_2$. Under these conditions 2000 g (20.4 tool) of N-formylalanine nitrile were metered in over a period of 10 h and stirring was continued for a further 12 h under 250 bar of $H_2$.

After cool-down and pressure-release, the effluent was filtered through a combined pressure/suction filter and concentrated in vacuo. There were obtained 1980 g (95%) of crude product having a purity of 96% (GC).

A product having a purity of better than 99% was obtained by continuous thin layer distillation (bp 115° C./0.3 mbar). Such purification is unnecessary, however, for the following cyclization/dehydrogenation.

EXAMPLE 2

Preparation of 4-methylimidazole from N-formyl-1,2-propanediamine

In an electrically heated fixed bed reactor having a capacity of 250 mL there were packed 200 mL of a catalyst, which consisted of 0.5% Pd on 80% $Al_2O_3$ and 20% CaO. The catalyst was activated for a period of 12 h at 350° to 375° C. in a stream of hydrogen (ca30L/h).

Then 100 g/h of a mixture, which consisted of 50% water and 50% N-formyl-1,2-propanediamine, were passed over the catalyst in vapor form at atmospheric pressure, together with ca50L/h of hydrogen at 350° to 375° C. The effluent was condensed and collected, and after ca 3 h 280 g of crude product was obtained, which was fractionally distilled in a packed column having a diameter of 20 cm. There were obtained 11 5.7 g (96%) of 4-methylimidazole; bp 136° to 140° C./ 12 mbar; > 99% (GC), which solidified to form a colorless substance on cooling.

The total yield from Examples 1 and 2 was approximately 91.2%.

EXAMPLE 3

Example 2 was repeated except that the catalyst packing consisted of a catalyst composed of 50% CuO and 50% Al$_2$O$_3$. From 50 g/h of N-formylalanine nitrile (no solvent) there were obtained after a period of 3h 135g of crude product. Fractional distillation thereof yielded 117.9 g (97.8%) of 4-methylimidazole having a purity better than 99% (GC). This is equivalent to a total yield (including Example 1) of 92.9%.

EXAMPLE 4

Example 3 was repeated except that the catalyst packing consisted of a catalyst composed of 80% ZnO and 20% Al$_2$O$_3$. The catalyst was not reduced before use. Following an on-stream period of 3 h under the conditions used in Example 3 there were obtained on completion of distillation 102.3 g (84.9%) of 4-methylimidazole having a purity better than 99% (GC). This is equivalent to a total yield (including Example 1) of 80.7%.

We claim:

1. A process for the preparation of a 4-substituted imidazole of the formula I

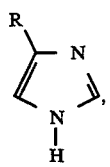

in which
R denotes C$_1$–C$_{20}$ alkyl, C$_3$–C$_{20}$ cycloalkyl, aryl, or C$_7$–C$_{20}$ aralkyl,
wherein
a) an N-formyl-α-aminonitrile of the formula II

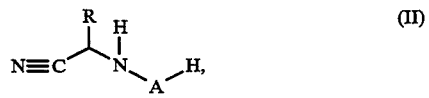

in which R has the meanings stated above and A stands for carbonyl, is reacted, at a temperature ranging from 20° to 200° C. and a pressure ranging from 20 to 500 bar, with hydrogen in the presence of a hydrogenation catalyst and b) the resulting N-formyl-1,2-diamine of the formula III

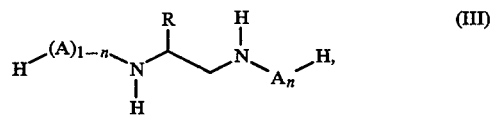

in which R and A have the meanings stated above and n stands for 0 or 1, is reacted over a cyclization/dehydrogenation catalyst at a temperature ranging from 200° to 600° C. and a pressure ranging from 0.001 to 5 bar.

2. A process for the preparation of a 4-substituted imidazole I as defined in claim 1, wherein hydrogenation catalysts are used which contain Fe, Co, Ni, Pd, Pt, Rh, and/or Ru as catalytically active substance(s).

3. A process for the preparation of a 4-substituted imidazole I as defined in claim 1, wherein a cyclization/dehydrogenation catalyst containing one or more Group IVb, Vb, VIb, VIIb, VIII, Ib, and IIb elements in the periodic table is used.

4. A process for the preparation of a 4-substituted imidazole I as defined in claim 1, wherein the N-formyl-α-aminonitrile II, in which R stands for methyl, is hydrogenated in the liquid phase using an Fe, Co and/or Ni catalyst and is then cyclized and dehydrogenated in the gas phase over a catalyst which contains one or more elements selected from the group consisting of Fe, Co, Ni, Pd, Pt, Cu, Ag, Zn, Cr, and Mo.

* * * * *

UNITED STATES PATENT AND TRADEMARK OFFICE
CERTIFICATE OF CORRECTION

PATENT NO.: 5,359,082

DATED: October 25, 1994

INVENTOR(S): KOEHLER et al.

It is certified that error appears in the above-identified patent and that said Letters Patent is hereby corrected as shown below:

Claim 1, column 5, line 42:
"aminonitrile" is unreadable on the printed patent due to a smudge.

Signed and Sealed this

Thirteenth Day of December, 1994

Attest:

BRUCE LEHMAN

Attesting Officer     Commissioner of Patents and Trademarks